(12) United States Patent
Broadus

(10) Patent No.: US 6,402,319 B1
(45) Date of Patent: Jun. 11, 2002

(54) ACQUISITION OF MULTIPLE EYE TOPOGRAPHY EXAMS

(75) Inventor: Charles R. Broadus, Ogden, UT (US)

(73) Assignee: Bausch & Lomb Incorporated, Rochester, NY (US)

(*) Notice: Subject to any disclaimer, the term of this patent is extended or adjusted under 35 U.S.C. 154(b) by 0 days.

(21) Appl. No.: 09/534,095

(22) Filed: Mar. 23, 2000

(51) Int. Cl.[7] .................................................. A61B 3/10
(52) U.S. Cl. ....................................................... 351/212
(58) Field of Search .................................. 351/205, 206, 351/212, 221; 606/5

(56) References Cited

U.S. PATENT DOCUMENTS 5,943,116 A * 8/1999 Zeimer ........................ 351/221

* cited by examiner

Primary Examiner—George Manuel
(74) Attorney, Agent, or Firm—Michael L. Smith

(57) ABSTRACT

An eye evaluation system includes an eye evaluating device (12) that acquires at least two exams of a patient's eye. The exams are a measure of some aspect of a patient's vision. An algorithm (FIG. 2) then compares the exams to determine if the exams are acceptable.

22 Claims, 2 Drawing Sheets

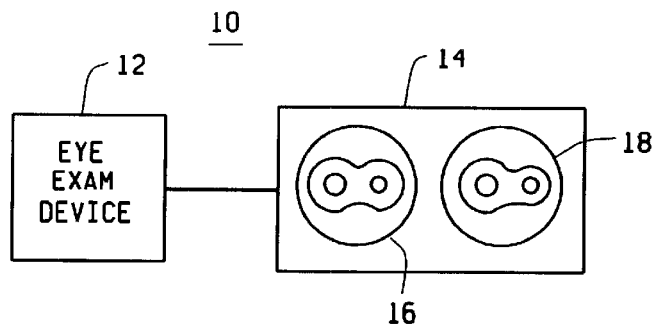
FIG. 1
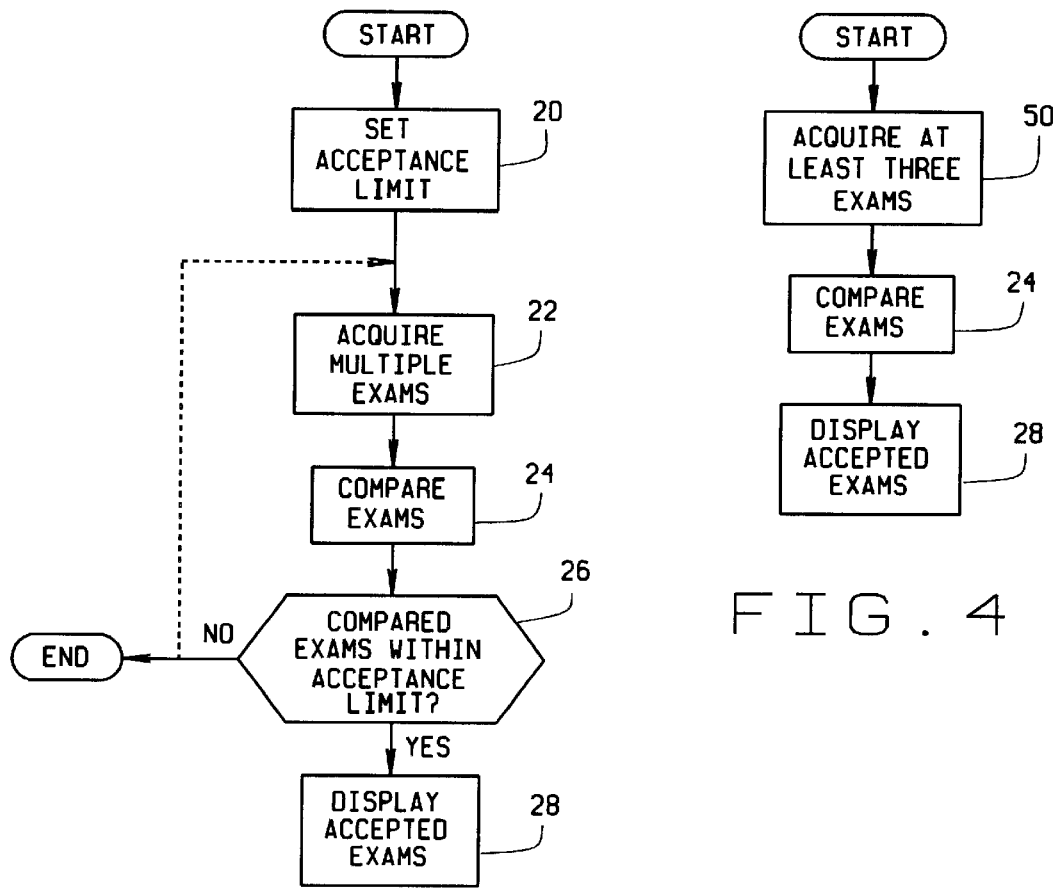
FIG. 2
FIG. 4

ACQUISITION OF MULTIPLE EYE TOPOGRAPHY EXAMS

FIELD OF THE INVENTION

The present invention relates to assuring a physician that acceptable eye exams have been acquired. More specifically, the present invention relates to assuring acceptable eye topography exams have been acquired by comparing multiple exams.

RELATED ART

Various corneal topography systems and methods are well known and described in the patented arts and in publications, such as *Corneal Topography: The State of the Art* by Gills, et al., published by Slack, Inc. (1995). The various systems and methods all provide a physician with information concerning a patient's vision defects. A variety of new topography systems, pachymetry systems, wavefront sensors, and general refractive error detection systems can detect the amount of myopia, hyperopia, and astigmatism, and also, higher order aberrations of the refractive characteristics of the eye.

This vision defect data, assists the physician in determining a patient's vision aberrations and the patient's need for and amount of vision correction. The range of vision correction options includes eyeglasses, contact lenses, or intraocular lenses, and various forms of refractive surgery. Refractive surgery techniques include LASIK (Laser-Assisted In-Situ Keratomileusis), PRK (photorefractive keratectomy), ALK (automated lamellar keratectomy), and LTK (laser thermal keratoplasty). All of these techniques aim to provide permanent vision correction.

In the event a LASIK procedure is desired, a physician or more likely a laser system develops an ablation profile for each patient's eye. The ablation profile defines the amount and location of corneal tissue to be removed from the patient's eye by the laser system. Laser surgical treatments have become progressively more refined, allowing more subtle defects to be corrected. Myopia and hyperopia can now be corrected to a high degree of precision with current techniques, and using excimer lasers, higher order defects can also be corrected, such as irregular astigmatism.

With the advance of refractive surgery, a fast developing area is what could properly be called "customized ablation". Customized ablation is where a LASIK or other refractive procedure is performed based upon an ablation profile generated for each individual patient's vision defects. It is believed that this customized ablation will result in better results for the patient than have been known in the prior art and will also significantly reduce the number of poor results. An example of a system employing a topography system in conjunction with a laser to generate an ablation profile is described in U.S. Pat. No. 5,891,132, entitled *Distributed Excimer Laser Surgery System*, issued Apr. 6 1999.

The accuracy of prior art exams has been determined by visual inspection of one or more exam by a physician. Another tool used in the prior art to assist the physician in choosing an exam to use is a difference map. A difference map is a graphical map showing the difference between to exams. The physician can then look at each individual exam and the difference maps to determine what exam, if any, to use for further treatment.

In preparing these customized ablation profiles, the topography data and other vision defect data will be heavily relied upon. Therefore, a need exists to assure that the data relied upon are accurate.

BRIEF DESCRIPTION OF THE DRAWINGS

FIG. 1 is a block diagram of a system in accordance with the present invention;

FIG. 2 is a flow diagram in accordance with a preferred embodiment of the present invention;

FIG. 4 is a flow diagram in accordance with an alternate embodiment of the present invention.

DETAILED DESCRIPTION OF THE PREFERRED EMBODIMENTS

Figure 3:
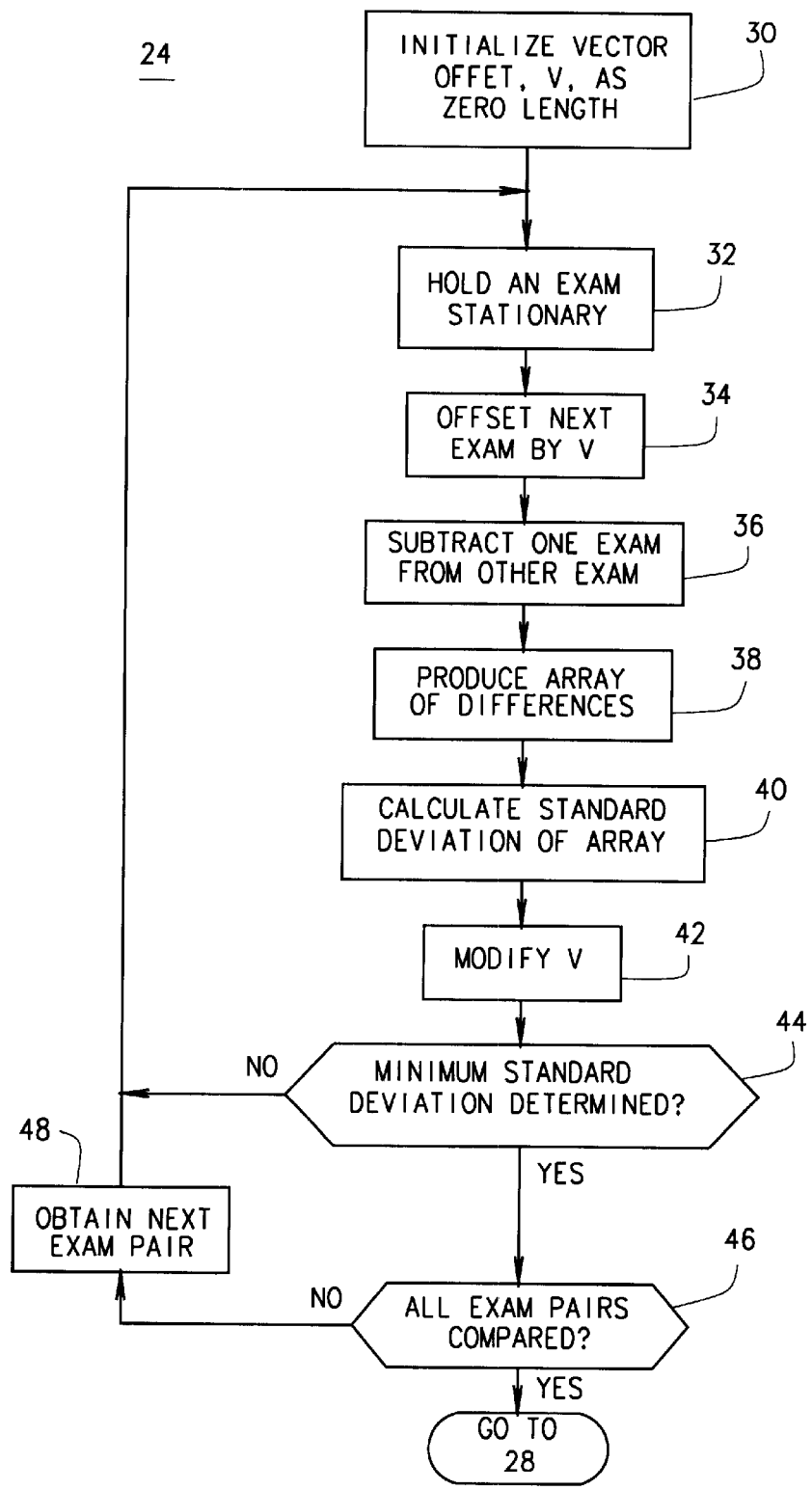
FIG. 3 is a flow diagram of a portion of FIG. 2 and FIG. 4.

FIG. 1 shows an eye exam system 10, in accordance with the present invention. The system 10 includes an eye exam device 12 and a display 14 for displaying data and graphical representations of an eye exam such as 16 and 18.

Eye exam device 12 is preferably an eye topography device such as an ORBSCAN® System available from Bausch & Lomb Surgical, Inc., though other known eye topography systems or other eye exam devices known in the art could be used. For example, device 12 could also be a curvature-based topography system, pachymetry system, wavefront sensor, or other vision error detection system, all of which are well known in the art. For illustrative descriptions of the elevation-based ORBSCAN topography system, see U.S. Pat. Nos. 5,512,965 and 5,512,966 by Richard K. Snook. Whatever specific device 12 is used it is important that the acquisition of acceptable, accurate exams is assured. As described in detail below, the present invention provides the assurance that more accurate and acceptable exams are used in treating a patient's eye.

Device 12 also preferably includes a memory (not shown) for acquiring and storing multiple eye exams. The display 14 may be any commonly known display suitable for graphics and text. Eye exams 16 and 18 are each examples of an exam of a patient's eye that are being displayed for use by a physician treating the patient's eye. The physician preferably chooses between eye exam 16 and 18 for use in treating the patient's eye, such as for creating a customized ablation profile as described above. Preferably, exams 16 and 18 are only displayed if the exams are acceptable, as further defined below. If no exams are acceptable, preferably, an appropriate message such as "No acceptable exams. Please acquire exams again." is displayed on display 14.

Eye exam device or eye evaluation system 12 also preferably includes an algorithm for comparing the exams to determine if the exams are acceptable. Because these exams are to be used to treat and correct a patient's vision, particularly where the exams are used to create a customized ablation profile, it is obvious that the physician needs to be confident that the exams are accurate and acceptable.

The preferred algorithms for comparing the exams will be discussed in relation to FIGS. 2–4 below. There are essentially two preferred methods where one method can be used with or without a defined acceptance limit.

More specifically, one preferred method described in detail below at FIG. 2 involves eye exam device 12 acquiring two exams. These two exams are then compared against each other and if the exams are within a predetermined acceptance limit the exams are accepted and then preferably displayed on display 14. The physician then chooses which exam to use to further treat the patient, such as for developing an ablation profile.

If the two exams are not within the predetermined acceptance limit, a message such as described above is preferably displayed, indicating that new exams need to be acquired. If the two exams are within the acceptance limit both exams can be said to be acceptable and accurate because the odds of two poor and inaccurate exams being within the acceptance limit would be so low as to be statistically insignificant. The acceptance limit is preferably obtained through the acquisition of a statistically significant number of eye exams and is determined by a number of factors such as the comparison of the exam deviation, comparison of results between similar devices, and the resulting patient outcomes.

If more than two exams are acquired the preferred algorithm for comparing the exams may be used with or without an acceptance limit. If three or more exams are acquired, preferably each exam is compared against each of the other exams. So, for example, when three exams are acquired three comparisons will be made between the first and second exam, the first and third exam, and the second and third exam. If four exams are acquired there would be six comparisons, and if five exams are acquired there would be ten comparisons and so on. If an acceptance limit is used then all exam pairs within the set limit may be displayed to the physician or preferably only the exam pair with a minimum deviation would be displayed. Where three or more exams are acquired and an acceptance limit is not used, preferably the two exams with the lowest minimum deviation are displayed to the physician. The physician then needs to review the exams to determine which exam, if any, to use for further treatment.

FIG. 2 shows a preferred method and operation of system 10 for determining if eye exams taken of a patient's eye are acceptable. FIG. 2 begins with step 20 where an acceptance limit is set. At present, it is believed that if a topographer such as an ORBSCAN System is used as exam device 12, that the acceptance limit should be set in the range of about 3 microns within the central optic zone. This range is simply an estimate. To achieve an accurate acceptance limit evaluation of test data for a particular type of exam device 12 will need to gathered and evaluated. Step 22 then acquires multiple exams, which may be as few as two exams of a patient's eye. The exams of the patient's eye are a measure of at least some aspect of a patient's vision and in the case of the preferred ORBSCAN System are a representation of at least the anterior corneal surface of the patient's eye. Said another way, the exam is a measure of the topography of an anterior surface of a patient's cornea. The eye exam device 12 may perform significant other measurements and exams of the eye beyond the topography of the patient's anterior corneal surface as is true with the preferred ORBSCAN System. These other measurements of the device 12 may be put on hold until an acceptable exam pair is found using the present invention or the physician chooses a particular exam. This can reduce the amount of computation time required of the device 12 to produce a full exam of a patient's eye. At this point, the acquired multiple exams are preferably stored in the memory of device 12.

Next, step 24 compares the acquired exams. Step 24 is described in detail below at FIG. 3. Preferably, step 24 uses a simplex algorithm of the type disclosed in *Numerical Recipes in C: The Art of Scientific Computing*, by William H. Press, et al., published by Cambridge University Press, 1992. Numerous other algorithms could also be used such as Random Walk, or brute force, trial and error methods. Step 26 then determines if the compared exams are within the acceptance limit. If the compared exams are not within the acceptance limit the algorithm can then end or loop back to step 22 to reacquire new exams, as indicated by the dashed line in FIG. 2.

If the compared exams are within the acceptance limit the accepted exams are preferably displayed on display 14 at step 28 for the physician to choose which exam to use.

Step 24 for comparing the exams is shown in detail in FIG. 3. Step 24 will be described in detail with respect to exams obtained from the preferred ORBSCAN System, which measures a topography of at least the anterior surface of a patient's cornea. It is to be understood that other algorithms for comparing the eye exams may be used depending upon the type of eye exam device 12 that is being used by the physician. Topography of a patient's cornea that is obtained by the preferred ORBSCAN System is a three-dimensional map of the elevation of the anterior surface of the cornea.

Step 30 initializes a vector offset, V, as a zero length three-dimensional vector. Vector V will be modified and used to offset one exam from another so that they may be compared. Step 32 then holds one exam stationary and step 34 offsets the next exam by vector V, which is initially a zero length three-dimensional vector. Step 36 subtracts one exam from the other on a point-by-point basis at several points along the surface. Next, step 38 produces an array of differences from the results of step 36.

Step 40 calculates the standard deviation of the array of step 38. Next step 42 modifies vector offset V. Preferably, V is modified by the selected algorithm such that a rapid solution is determined as described in Step 44.

Step 44 then determines if a minimum standard deviation has been determined. If a minimum standard deviation has not been determined the process loops back to step 32. A minimum standard deviation is preferably determined by the selected algorithm. Preferably, the algorithm efficiently retains the minimum standard deviation and its associated offset vector V, and determines a new V to search for a lower standard deviation.

If a minimum standard deviation has been determined for a pair of exams, step 46 then determines if all exam pairs have been compared. If exam pairs remain to be compared, step 48 obtains the next exam pair before proceeding back to step 32. If all exam pairs have been compared the process goes to step 28 for displaying the accepted exams. As previously stated, the accepted exams displayed could be all accepted exams or only the exam pair with a lowest minimum standard deviation. The exam pair with the lowest minimum standard deviation could be said to be the best and most accurate exam pair.

FIG. 4 discloses an alternate embodiment in accordance with the present invention where, at step 50, device 12 acquires at least three exams and then step 24 compares the acquired exams as described above in FIG. 3. Step 28 then displays the accepted exams, which are preferably the exam pair with a lowest minimum standard deviation.

Thus, there has been shown and described an inventive eye evaluation system and method for assuring that acceptable and accurate eye exams have been obtained. Other embodiments of the present invention may fall within the scope of the claims, as will be readily apparent by those skilled in the art.

What is claimed is:

1. An eye evaluation system comprising:
   an eye evaluating device for acquiring at least two exams of a patient's eye wherein the exams are a measure of some aspect of a patent's vision; and
   an algorithm for comparing the exams to determine if the exams are acceptable;
   wherein the algorithm further includes, means for offsetting one of the exams relative to the other exam by a three-dimensional vector;

means for subtracting one exam from the other exam at several points on the anterior surface to produce an array of differences;

means for calculating a standard deviation of the array;

means for determining a minimum standard deviation;

means for accepting the two eye exams if the minimum standard deviation is less than or equal to a predetermined acceptable standard deviation; and means for rejecting the two eye exams if the minimum standard deviation is greater than the acceptable standard deviation.

2. A method of determining the acceptability of eye topography exams comprising the steps of:

acquiring at least two exams of a patient's eye wherein each exam is at least a measure of a topography of an anterior surface of a patient's cornea;

comparing each exam against the other exams; and accepting each pair of exams having a comparison within a predetermined acceptance limit.

3. The method of claim 2 further including the step of displaying the accepted exams for use by a physician in treating the patient's eye.

4. The method of claim 2 wherein the acquiring step further includes the steps of:

using an eye topography device, such as an ORBSCAN System, for acquiring the exams; and storing each exam in a memory of the device.

5. The method of claim 2 wherein the comparing step further includes the steps of:

(a) offsetting each exam relative to the other exams by a three-dimensional vector;

(b) subtracting each exam for the other exams at several points on the anterior surface to produce an array of differences;

(c) calculating a standard deviation of the array; and (d) repeating steps (a)–(c) to determine a minimum standard deviation for each pair of exams.

6. The method of claim 5 wherein the accepting step further includes accepting each pair of exams whose minimum standard deviation is less than or equal to a predetermined acceptable standard deviation.

7. The method of claim 5 further including the step of accepting the pair of exams with the lowest minimum standard deviation.

8. A method of determining the acceptability of eye topography exams comprising the steps of:

(a) acquiring at least three exams of a patient's eye wherein each exam is at least a measure of a topography of an anterior surface of a patient's cornea;

(b) comparing each exam against the other exams to produce a comparison result for each pair of exams;

(c) accepting each pair of exams having a comparison result within a predetermined acceptance limit;

(d) displaying at least one pair of exams accepted in step (c) for use by a physician in treating the patient's eye; and (e) displaying a message to start the method again if no pair of exams was accepted in step (c).

9. The method of claim 8 wherein the acquiring step further includes the steps of:

using an eye topography device, such as an ORBSCAN System, for acquiring the exams; and storing each exam in a memory of the device.

10. The method of claim 8 wherein step (b) further includes the steps of:

(b1) offsetting each exam relative to the other exams by a three-dimensional vector;

(b2) subtracting each exam for the other exams at several points on the anterior surface to produce an array of differences;

(b3) calculating a standard deviation of the array; and (b4) repeating steps (b1)–(b3) to determine a minimum standard deviation for each pair of exams.

11. The method of claim 10 wherein step (c) further includes accepting each pair of exams whose minimum standard deviation is less than or equal to a predetermined acceptable standard deviation.

12. The method of claim 11 wherein step (d) further includes the step of displaying the pair of exams with a lowest standard deviation.

13. A method of accepting eye topography exams, for use by a physician in treating a patient's eye, comprising the steps of:

acquiring at least three exams of the patient's eye wherein each exam is at least a measure of a topography of an anterior surface of a patient's cornea;

comparing each exam with the other exams to produce a comparison result for each exam pair; and accepting the exam pair having the comparison result indicating that the accepted exam pair are most similar to each other relative to the other exam pairs.

14. The method of claim 13 further including the step of displaying the accepted exam pair for use by the physician.

15. The method of claim 13 wherein the acquiring step further includes the steps of:

using an eye topography device, such as an ORBSCAN System, for acquiring the exams; and storing each exam in a memory of the device.

16. The method of claim 13 wherein the comparing step further includes the steps of:

(a) offsetting each exam relative to the other exams by a three-dimensional vector;

(b) subtracting each exam for the other exams at several points on the anterior surface to produce an array of differences;

(c) calculating a standard deviation of the array; and (d) repeating steps (a)–(c) to determine a minimum standard deviation for each pair of exams.

17. The method of claim 16 wherein the accepting step further includes accepting the exam pair with the lowest minimum standard deviation.

18. The method of claim 17 wherein the accepting step still further includes accepting the lowest minimum standard deviation exam pair whose minimum standard deviation is less than or equal to a predetermined acceptable standard deviation.

19. A method of accepting eye topography exams, for use by a physician in treating a patient's eye, comprising the steps of:

acquiring at least three exams of the patient's eye wherein each exam is at least a measure of a topography of an anterior surface of a patient's cornea;

comparing each exam with the other exams to produce a minimum standard deviation for each exam pair; and accepting the exam pair with the lowest standard deviation.

20. The method of claim 19 further including the step of displaying the accepted exam pair for use by the physician.

21. The method of claim 20 wherein the acquiring step further includes the steps of:

using an eye topography device, such as an ORBSCAN System, for acquiring the exams; and storing each exam in a memory of the device.

22. The method of claim 21 wherein the comparing step further includes the steps of:
   (a) offsetting each exam relative to the other exams by a three-dimensional vector;
   (b) subtracting each exam from the other exams at several points on the anterior surface to produce an array of differences for each exam pair;
   (c) calculating a standard deviation of the array;
   (d) modifying the three-dimensional vector; and
   (e) repeating steps (a)–(d) until a minimum standard deviation for each exam pair is determined.

* * * * *